United States Patent [19]
Baxter et al.

[11] Patent Number: 5,994,293
[45] Date of Patent: Nov. 30, 1999

[54] PEPTIDYL COMPOUNDS AND THEIR THERAPEUTIC USE

[75] Inventors: Andrew Douglas Baxter; John Montana; David Alan Owen, all of Cambridge, United Kingdom

[73] Assignee: Darwin Discovery Ltd., United Kingdom

[21] Appl. No.: 08/644,381

[22] Filed: May 10, 1996

[30] Foreign Application Priority Data

May 10, 1995 [GB] United Kingdom ............... 9509404
Dec. 15, 1995 [GB] United Kingdom ............... 9525646
Apr. 4, 1996 [GB] United Kingdom ............... 9607154

[51] Int. Cl.$^6$ .................... C07K 5/00; A61K 38/05
[52] U.S. Cl. ................... 514/2; 514/19; 530/331; 530/868; 424/184.1; 424/185.1; 260/998.2
[58] Field of Search ............. 514/2, 19; 530/868, 530/331; 260/998.2; 424/184.1, 185.1

[56] References Cited

U.S. PATENT DOCUMENTS 5,144,043  9/1992  Dean et al. ............... 548/548
5,214,181  5/1993  Morita et al. ............ 558/248

FOREIGN PATENT DOCUMENTS

| 8806890 | 9/1988 | WIPO . |
| 9320047 | 10/1993 | WIPO . |
| 9409128 | 4/1994 | WIPO . |
| 9506031 | 3/1995 | WIPO . |
| 9509841 | 4/1995 | WIPO . |
| 9513289 | 5/1995 | WIPO . |

OTHER PUBLICATIONS

Spatola, "Chemistry & Biochemistry of Amino Acids, Peptides, Proteins" vol. 7 (Marcell Decker Inc 1983) pp. 277–281, 338–340.

Fournie–Zaluski et al. Eur. J. Biochem. vol. 139 pp. 267–274 (1984).

*Primary Examiner*—Bennett Celsa
*Attorney, Agent, or Firm*—Saliwanchik, Lloyd & Saliwanchik

[57] ABSTRACT

Dipeptidyl derivatives having a SH of acylS group and which are amides, thioamides or $S(O)_{0-2}$-amides, have therapeutic utility via MMP or TNF inhibition.

29 Claims, No Drawings

PEPTIDYL COMPOUNDS AND THEIR THERAPEUTIC USE

FIELD OF THE INVENTION

This invention relates to a novel class of peptidyl derivatives, to processes for their preparation, and to their use in medicine.

BACKGROUND OF THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least four groups of metalloproteinases. These are the collagenases (interstitial collagenase, MMP-1; PMN collagenase, MMP-8, collagenase -3, MMP-13), the gelatinases (gelatinase A, MMP-2, 72 kDa-gelatinase, Type IV collagenase; gelatinase B, MMP-9, 92 kDa-gelatinase, Type IV collagenase) the stromelysins (proteoglycanase, MMP-3, stromelysin-1, transin; stromelysin-2, MMP-10; stromelysin 3, MMP-11) and the membrane type matrix metalloproteinases (MT-1, MMP-14; MT-2, MMP-15; MT-3, MMP-16 and MT-4, MMP-17). Normally these catabolic enzymes are tightly regulated at the level of their synthesis and secretion and also at the level of their extracellular activity, the latter through the action of specific inhibitors, such as TIMP (tissue inhibitors of metalloproteinase), which form inactive complexes with metalloproteinases, and more general proteinase inhibitors such as $a_2$-macroglobulins.

The accelerated, uncontrolled breakdown of connective tissues by metalloproteinase catalysed resorption of the extracellular matrix is a feature of many pathological conditions such as rheumatoid arthritis, osteoarthritis, septic arthritis, corneal, epidermal or gastric ulceration; tumour metastasis or invasion; periodontal disease, proteinuria, coronary thrombosis associated with atherosclerotic plaque rupture and bone disease. Inhibitors may also be useful in preventing the pathological squaelae following a traumatic injury that could lead to a permanent disability. These compounds may also have utility as a means for birth control by preventing ovulation or implantation. It can be expected that the pathogenesis of such diseases is likely to be modified in a beneficial manner by the administration of metalloproteinase inhibitors and numerous compounds have been suggested for this purpose [for a general review see R. C. Wahl, et al Ann. Rep, Med. Chem. 25: 175–184, Academic Press Inc., San Diego (1990)].

A number of small peptide like compounds which inhibit metalloproteinases have been described. Perhaps the most notable of these are those relating to angiotensin converting enzyme (ACE) where such agents act to block the conversion of the decapeptide angiotensin I to angiotensin II, a potent pressor substance. Compounds of this type are described in EP-A-0012401. Also, related mercaptoamide peptidyl derivatives have shown ACE inhibitor activity in vitro and in vivo (H N Weller et al (1984), Biochem Biophys. Res. Comm., 125 (1):82–89).

TNF is a cytokine which is produced initially as a cell-associated 28kD precursor. It is released as an active, 17kD form (D-M Jue et al, (1990) Biochemistry, 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal heamatopoiesis in patients with these tumours.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al (1988) J. Clin. Invest. 81:1925–1937; Miethke et al (1992), J. Exp. Med. 175:91–98), post ischaemic reperfusion injury, malaria (Grau et al (1989), Immunol. Rev. 112:49–70); mycobacterial infection (Barnes et al (1992) Infect. Imm. 60:1441–6), meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Current clinical anti-TNF strategies involve the use of corticosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNF gene transcription (Endres S. (1991) Immunol. 72:56–60, Schandene et al (1992), Immunol. 76:30–34, Alegre M L, et al (1991); Transplantation 52:674–679, Bianco et al (1991) Blood 78: 1205–1221). Thalidomide has also been shown to inhibit TNF production by leucocytes (Sampajo et al (1991), J. Exp. Med. 173:699–703). In experimental settings, anti-TNF monoclonal antibodies, soluble TNF receptors and soluble TNF receptor/immunoadhesins have been shown to specifically inhibit the effects of TNF action (Bagby et al (1991) J. Infect. Dis. 163:83–88, Charpentier et al. (1991) Pressemed. 20:2009–2011, Silva et al (1990) J. Infect. Dis. 1β:421–427; Franks et al (1991) Infect. Immun. 59:2609–2614, Tracey et al (1987) Nature330:662–664; Fischer et al (1992) PNAS U.S.A. in press, Lesslauer et al (1991) Eur. J. Immunol. 21:2883–2886, Ashkenazi et al (1991) PNAS U.S.A. 88:10535–10539).

It has recently been shown that the effects of TNF are mediated by two peptides, TNFα and TNFβ. Although these peptides have only 30% homology with each other, they activate the same receptors and are encoded by immediately adjacent genes. As used herein, the term tumour necrosis factor or TNF therefore means tumour necrosis factor a and peptides having a high degrees of sequence homology with, or substantially similar physiological effects to, TNFα, for example TNFβ.

One of the objectives of the present invention is to provide compounds which substantially inhibit the release of TNF from cells, and therefore may be used in the treatment of conditions mediated by TNF. Such uses include, but are not limited to, the treatment of inflammation, fever, cardiovascular effects, haemorrhage, coagulation and acute phase response, cachexia and anorexia, acute infections, shock states, graft versus host reactions and autoimmune disease.

Compounds which have the property of inhibiting the action of metalloproteinases involved in connective tissue breakdown such as collagenase, stromelysin and gelatinase have been shown to inhibit the release of TNF both in vitro and in vivo (A J H Gearing et al (1994), Nature, 370:555–557; G M McGeehan et al (1994), Nature, 370:558–561: M J Crimmin et al, WO 93/20047). All of these reported inhibitors contain a hydroxamic acid zinc binding group.

It is, therefore, a further objective of this invention to provide compounds which, in addition to inhibiting TNF release, also inhibit the action of MMPs, and hence may be used in the treatment of patients who suffer from conditions mediated by TNF and/or MMPs.

As appreciated by those of skill in the art the significant proportion of homology between human fibroblast collagenase, stromelysin and gelatinase leads to the possibility that a compound that inhibits one enzyme may to some degree inhibit all of them.

Compounds that inhibit collagenase, which possess structural portions akin to those of the instant invention include those encompassed by U.S. Pat. No. 4,511,504 issued Apr. 16, 1985; U.S. Pat. No. 4,568,666, issued Feb. 4, 1986.

Compounds of related structure that are claimed to inhibit stromelysin (proteoglycanase) are encompassed by U.S. Pat. No. 4,771,037, issued Sep. 13, 1988.

The applicants believe that stromelysin and collagenase inhibitors have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case et al (1989), J. Clin. Invest., 84:1731–40; R. J. Williams et al (1990), Arth. Rheum., 33: 533–41.

The applicants also believe that inhibitors of stromelysin, collagenase and gelatinase will be useful to control tumour metastasis, optionally in combination with current chemotherapy and/or radiation. See L. M. Matrisian et al (1986), Proc. Natl. Acad. Sci., U.S.A., 83:9413–7; S. M. Wilhelm et al (1987), Ibid. 84:6725–29; Z. Werb et al (1989), J. Cell Biol., 109:872–889; L. A. Liotta et al (1983), Lab. Invest., 49:636–649; R. Reich et al in Metatasis; Ciba Foundation Symposium, Wiley, Chicester, 1988, pp. 193–210.

Secreted proteinases such as stromelysin, collagenase and gelatinase play an important role in processes involved in the movement of cells during metastasic tumour invasion. Indeed, there is also evidence that the matrix metalloproteinases are overexpressed in certain metastatic tumour cell lines. In this context, the enzyme functions to penetrate underlying basement membranes and allow the tumour cell to escape from the site of primary tumour formation and enter the circulation. After adhering to blood vessel walls, the tumour cells use these same metalloproteinases to pierce underlying basement membranes and penetrate other tissues, thereby leading to tumour metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts derived from inflamed gingiva (V. J. Uitto et al (1981), J.Periodontal Res., 16:417–424). Enzyme levels have been correlated to the severity of gum disease; C. M. Overall et al (1987), J. Periodontal Res., 22:81–88.

Proteolytic processes have also been observed in the ulceration of the cornea following alkali burns (S. I. Brown et al (1969), Arch. Opthalmol., 81:370–373). Mercapto-containing peptides do inhibit the collagenase isolated from alkali-burned rabbit cornea (F. R. Burns et al (1989), Invest. Opthalmol, 30: 1569–1575). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine (W. H. Baricos et al (1989), Biochem. J., 254:609–612). Proteinuria, a result of glomerular disease, is excess protein in the urine caused by increased permeability of the GBM to plasma proteins. The underlying causes of the increased GBM permeability are unknown, but proteinases including stromelysin may play an important role in glomerular diseases. Inhibition of this enzyme may alleviate the proteinura associated with kidney malfunction.

It is suggested that inhibition of matrix metalloproteinase activity may prevent the rupturing of atherosclerotic plaques leading to coronary thrombosis. The tearing or rupture of atherosclerotic plaques is the most common event initiating coronary thrombosis. Destabilisation and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localised to individual cells in atherosclerotic plaques removed from heart transplant patients at the time of surgery (A. M. Henney et al (1991), Proc. Nat'l. Acad. Sci. U.S.A., 88:8154–8158). Inhibition of stromelysin by these compounds may aid in preventing or delaying the degradation of the connective tissue matrix that stabilises the atherosclerotic plaques, thereby preventing events leading to acute coronary thrombosis.

It has been recently shown in a model of congestive heart failure (CHF) in the pig, that during CHF the are marked changes in the morphological structure of the heart. Ventricular dilation and wall thinning caused by changes to the extracellular matrix results in fewer collagen connections between cardiomyocytes and less total collagen. In such an instance a weaker force of contraction leads to an inefficient ventricular operation. It is believed that specific inhibitors of matrix metalloproteinases will play a key role in stabilising the extracellular matrix and therefore be important in the treatment and/or prevention of CHF.

It has recently been shown (WO 96/0240) that inhibitors of the matrix metalloproteinases, such as collagenase and stromelysin also inhibit the formation of human soluble CD23. CD23 is a 45kDa type II integral protein expressed on the surface of a variety of mature cells, including B and T lymphocytes, macrophages, NK cells, Langerhans cells, monocytes, eosinophils and platelets (Delespesse et al, Adv. Immunology, 49, 1991, 149; Grangette et al, J., Immunol, 143, 1989, 3580). Several activities have been ascribed to soluble CD23 in man, all of which involve IgE regulation. Particular activities include:

i) antigen presentation ii) IgE mediated eosinophil cytotoxicity iii) B cell homing to lymph nodes and the spleen iv) downregulation of IgE synthesis Thus, overall the excessive production of soluble CD23 has been implicated in the overproduction of IgE, the hallmark of allergic diseases such as extrinsic asthma, rhinitis, allergic conjunctivitis, eczema, atopic dermatitis and anaphylaxis (Sutton et al, Nature, 366, 1993, 421). Elevated levels of soluble CD23 have also been observed in the serum of patients with chronic B lymphocytic leukaemia (Safarti et al, Blood, 71, 1988, 94), and in the synovial fluid of patients with rheumatoid arthritis (Chomarat et al, Arthritis and Rheumatism, 36, 1993, 234).

It is therefore, a further objective of the present invention to provide compounds which inhibit the formation of human soluble CD23 for the production of a medicament for the treatment or prophylaxis of disorders such as allergy and autoimmune disease in which the overproduction of soluble CD23 is implicated, such as those described above.

Recent reports suggest that new enzymes of the MMP family also mediate the shedding of adhesion molecules such as the selectins, such as L-selectin. These soluble adhesion molecules are implicated in a number of diseases including cancer, autoimmunity and in the inflammatory response. It has been proposed that once cleaved, the selectin bind to particular ligands and this accounts for their biological activity. Thus, drugs that interfere with or prevent binding of the ligands to the selectins will be useful medicaments for treating a variety of the diseases described above. Therefore, it is a yet further objective of the present invention to provide compounds which inhibit the shedding of certain adhesion molecules and thus provide the production of a medicament for the treatment or prophylaxis of disorders such as cancer, autoimmune diseases or inflammatory diseases (such as inflammatory bowel disease and multiple sclerosis).

It is also believed that specific inhibitors of stromelysin and collagenase should be useful as birth control agents. There is evidence that expression of metalloproteinases, including stromelysin and collagenase, is observed in unfertilised eggs and zygotes and at further cleavage stages and increased at the blastocyst stage of fetal development and with endoderm differentiation (C. A. Brenner et al (1989), Genes & Develop., 3:848–59). By analogy to tumour invasion, a blastocyst may express metalloproteinases in order to penetrate the extracelluar matrix of the uterine wall during implantation. Inhibition of stromelysin and collagenase during these early development processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation (J. F. Woessner et al (1989), Steroids, 54:491–499). There may also be a role for stromelysin activity during ovulation (C. K. L. Too et al (1984), Endocrin., 115: 1043–1050).

Collagenolytic and stromelysin activity have also been observed in dystrophic epidermolysis bullosa (A. Kronberger et al (1982), J. Invest. Dermatol., 79:208–211; D. Sawamura et al (1991), Biochem. Biophys. Res. Commun., 184:1003–8). Inhibition of metalloendoproteinases should limit the rapid destruction of connective components of the skin.

In addition to extracelluar matrix comprising structural components, stromelysin can degrade other in vivo substrates including the inhibitors $a_1$-proteinase inhibitor and may therefore influence the activities of other proteinases such as elastase (P. G. Winyard et al (1991), FEBS Letts., 279.1:91–94). Inhibition of the matrix metalloendoproteinases may potentiate the antiproteinase activity of these endogenous inhibitors.

From recent publications it is evident that several new enzymes of the MMP family have been identified, some of which may be important in disease. Collagenase 3, an enzyme found in breast carcinoma tissue may have utility in breast cancer (J M P Freije et al (1994), J. Biol. Chem., 269 (24): 16766–16773) and other disease states, such as arthritis, whilst MT-MMPs, other members of the MMP family have been shown to be key enzymes in the activation of gelatinase A (H Sato et al (1994), Nature, 370:61–65). Gelatinase A is an important enzyme in the growth and metastasis of tumours (such as defined above).

The degradation of β-Amyloid Precursor Protein (APP) has been shown to generate amyloid plaques, a major constituent of the senile plaques, found in patients with Alzheimers Disease (AD). Two recent publications have identified metalloproteinase enzymes that cleave APP to the amyloid plaque (C R Abraham et al (1994), Biochemistry, 33:192–199; G Huber et al (1994), Biochem. Biophys. Res. Comm., 201 (1):45–53).

As appreciated by those of skill in the art, the significant proportion of homology between these new enzymes and other MMPs leads to the possibility that a compound that inhibits one enzyme may to some degree inhibit these new enzymes. Therefore, inhibitors encompassed in this invention may be useful in the diseases in which these new enzymes are implicated.

SUMMARY OF THE INVENTION

The invention encompasses novel compounds of formula (I) which are useful inhibitors of matrix metalloproteinases and/or TNFα mediated diseases including degenerative diseases (such as defined above) and certain cancers.

In a first aspect of the invention there is provided a compound of general formula (I):

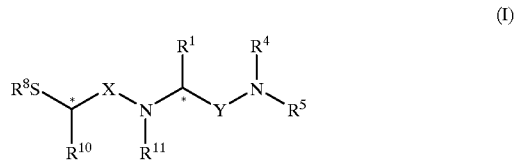

Wherein:

X and Y may be C=O or C=S and may be the same or different; Y may also be $S(O)_m$ where m=1–2;

$R^1$ is a $C_{1-6}$ alkyl, $C_{2-6}$ alkenyl, aryl, $C_{1-6}$ alkyl-aryl, heteroaryl, $C_{1-6}$ alkyl-heteroaryl, cyclo($C_{3-6}$)alkyl, $C_{1-6}$ alkyl-cyclo($C_{3-6}$)alkyl, heterocyclo($C_{4-6}$)alkyl, $C_{1-6}$ alkyl-heterocyclo($C_{4-6}$)alkyl, $C_{1-6}$ alkyl-COR$^2$, or $C_{1-6}$ alkyl-AR$^3$ group where A is O, NR$^3$ or $S(O)_n$ where n=0–2 and R$^3$ is H, $C_{1-4}$ alkyl, aryl, heteroaryl, $C_{1-4}$ alkyl-aryl or $C_{1-4}$ alkyl-heteroaryl; If A=NR$^3$ the groups R$^3$ may be the same or different.

$R^2$ is OR$^4$ or N(R$^4$)$_2$ where R$^4$ may be the same or different;

$R^4$ is H or $C_{1-4}$ alkyl;

$R^5$ is aryl (optionally substituted with R$^6$), heteroaryl (optionally substituted with R$^6$), $C_{1-4}$ alkyl-aryl (optionally substituted with R$^6$), $C_{1-4}$ alkyl-heteroaryl (optionally substituted with $R^6$), $C_{1-4}$ alkyl (substituted with $R^{21}$), cyclo($C_{3-6}$) alkyl (optionally substituted with $R^6$),$C_{1-4}$ alkyl-cyclo($C_{3-6}$)alkyl (substituted with $R^6$), heterocyclo($C_{4-6}$)alkyl (optionally substituted with $R^6$), or $C_{1-4}$ alkyl-heterocyclo($C_{4-6}$)alkyl (optionally substituted with $R^6$);

$NR^4R^5$ may form a ring such as a pyrrolidine (optionally substituted with $R^6$), piperidine (optionally substituted with $R^6$), morpholine (optionally substituted with $R^6$) or piperazines of the type:

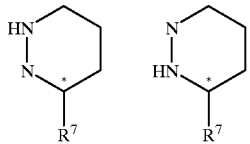

optionally substituted with $R^6$ at any available position.

$R^6$ is H, halogen, $C_{1-6}$ alkyl, aryl, heteroaryl, $OR^3$, $S(O)_nR^3$ where n=0–2, $NR^3R^7$, $COR^9$, $SO_2N(R^3)_2$ where $R^3$ maybe the same or different, $CON(R^3)_2$ where $R^3$ maybe the same or different, amidine or guanidine;

$R^7$ is $COR^9$, $CO_2R^{19}$, $SO_2R^9$ or $CO(NR^3)_2$ where $R^3$ maybe the same or different;

$R^8$ is H or the group $COR^9$;

$R^9$ is $C_{1-4}$ alkyl, aryl, heteroaryl, $C_{1-4}$ alkyl-aryl or $C_{1-4}$ alkyl-heteroaryl;

$R^{10}$ and $R^{11}$ may be the same or different taken from the groups, H, $C_{1-6}$ alkyl, (optionally substituted with $R^{12}$), aryl (optionally substituted with $R^{12}$), $C_{1-6}$ alkyl-aryl (optionally substituted with $R^{12}$), heteroaryl (optionally substituted with $R^{12}$), $C_{1-6}$ alkyl-heteroaryl (optionally substituted with $R^{12}$), cyclo($C_{3-6}$) alkyl (optionally substituted with $R^{12}$),$C_{1-6}$ alkyl-cyclo($C_{3-6}$)alkyl (optionally substituted with $R^{12}$), heterocyclo($C_{4-6}$) alkyl (optionally substituted with $R^{12}$) or $C_{1-4}$ alkyl-heterocyclo($C_{4-6}$)alkyl (optionally substituted with $R^{12}$);

$R^{12}$ is $SR^8$, $COR^{13}$, $NR^3R^{14}$ the group $AR^3$ where A is O, $NR^3$ or $S(O)_n$ where n=0–2, if A=$NR^3$ the groups $R^3$ may be the same or different, phthalimido or the groups:

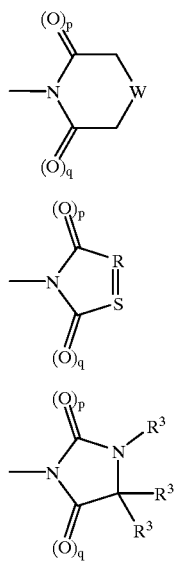

-continued

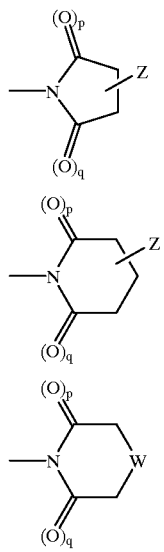

p and q may be 0 or 1 and may be the same or different;

R and S may be CH or N and may be the same or different;

W may be O, $S(O)_n$ where n=0–2 or $NR^{15}$;

Z may be H or $C_{0-4}$ alkyl-$R^{18}$ and may be attached to any available position on the ring;

$R^{13}$ is $OR^{20}$, $N(R^3)_2$ where $R^3$ maybe the same or different, $C_{1-4}$ alkyl, aryl, $C_{1-4}$ alkyl-aryl, heteroaryl or $C_{1-4}$ alkyl-heteroaryl;

$R^{14}$ may be any group defined in $R^7$, $SO_2R^{16}$, or $COR^{16}$;

$R^{15}$ is H, $C_{1-4}$ alkyl, $COR^9$, $CO_2R^{19}$, $CON(R^3)_2$ where $R^3$ maybe the same or different or $SO_2R^9$;

$R^{16}$ is $C_{1-4}$ alkyl (optionally substituted with $R^{17}$);

$R^{17}$ may be $CO_2R^3$, $CON(R^3)_2$ where $R^3$ maybe the same or different, $N(R^3)_2$ where $R^3$ maybe the same or different, $SO_2R^9$ or the groups:

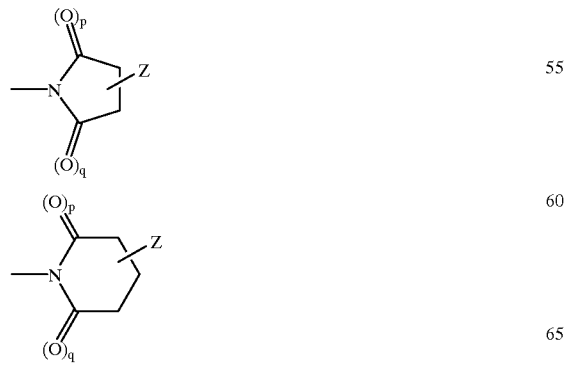

-continued

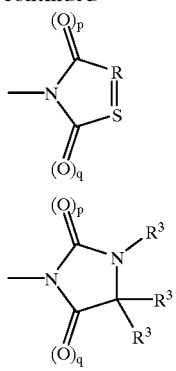

$R^{18}$ is $CO_2R^3$, $CON(R^3)_2$ where $R^3$ maybe the same or different, $N(R^3)_2$ where $R^3$ maybe the same or different, $NHCO_2R^{19}$, $NHSO_2R^9$ or $NHCOR^9$;

$R^{19}$ is $C_{1-4}$ alkyl, $C_{1-4}$ alkyl-aryl or $C_{1-4}$ alkyl-heteroaryl;

$R^{20}$ is H, $C_{1-4}$ alkyl, $C_{1-4}$ alkyl-aryl or $C_{1-4}$ alkyl-heteroaryl;

$R^{21}$ is $C_{1-6}$ alkyl, aryl, heteroaryl, $NR^3R^7$, $COR^9$, $SO_2N(R^3)_2$ where $R^3$ maybe the same or different, $CON(R^3)_2$ where $R^3$ maybe the same or different, amidine or guanidine;

and the salts, solvates and hydrates thereof.

Preferred compounds of the invention include those in which, independently or in any combination have:

X and Y is C=O $R^1$ is a $C_{1-6}$ alkyl or $C_{1-6}$ alkyl-$AR^3$ group where A is O, $NR^3$ or $S(O)_n$ where n=0–2 and $R^3$ is H, $C_{1-4}$ alkyl heteroaryl or aryl;

$R^4$ is H or $C_{1-4}$ alkyl;

$R^5$ is aryl (optionally substituted with $R^6$), heteroaryl (optionally substituted with $R^6$), $C_{1-4}$ alkyl-aryl (optionally substituted with $R^6$), $C_{1-4}$ alkyl-heteroaryl (optionally substituted with $R^6$) or $C_{1-4}$ alkyl-heterocyclo($C_{4-6}$)alkyl (optionally substituted with $R^6$);

$R^6$ is H, halogen, $C_{1-6}$ alkyl, aryl, heteroaryl, $OR^3$, $NR^3R^7$, $COR^9$, $SO_2N(R^3)_2$ where $R^3$ maybe the same or different, $CON(R^3)_2$ where $R^3$ maybe the same or different, amidine or guanidine;

$NR^4R^5$ is a ring such as a pyrrolidine (optionally substituted with $R^6$), piperidine (optionally substituted with $R^6$), morpholine (optionally substituted with $R^6$) or piperazines of the type:

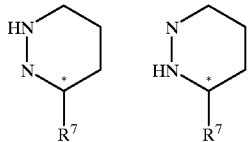

optionally substituted with $R^6$;

$R^7$ is $CO_2R^{19}$ or $CONHR^3$ where $R^{19}$ is H or $C_{1-4}$ alkyl;

$R^8$ is H or the group $COR^9$;

$R^9$ is $C_{1-4}$ alkyl or aryl;

$R^{11}$ is H;

$R^{10}$ is H, $C_{1-6}$ alkyl (optionally substituted with $R^{12}$), $C_{1-6}$ alkyl-aryl (optionally substituted with $R^{12}$) or $C_{1-6}$ alkyl-heteroaryl (optionally substituted with $R^{12}$);

$R^{12}$ is $SR^8$, $COR^{13}$, $NR^3R^7$, $N(R^3)_2$, $SO^2R^9$, phthalimido or succinimido;

$R^{13}$ is $OR^{20}$, $N(R^3)_2$ where $R^3$ maybe the same or different and $R^{20}$ is H or $C_{1-4}$ alkyl;

It will be appreciated that the compounds according to the invention can contain one or more asymmetrically substituted carbon atoms, for example those marked with an asterisk in formula (I). The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric centre to represent the of R- and S-configurations, the < line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including for example, methyl, ethyl, propyl, isopropyl, butyl, tert-butyl, pentyl, hexyl and the like.

The term "$C_{1-4}$ alkyl" refers to a straight or branched chain alkyl moiety having from one to four carbon atoms, including for example, methyl, ethyl, propyl, isopropyl , butyl, tert-butyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cyclo ($C_{3-6}$) alkyl" refers to a saturated alicyclic moiety having from three to six carbon atoms and includes for example cyclopropyl, cyclobutyl, cyclopentyl, cyclohexyl and the like.

The term "cyclo ($C_{4-6}$) alkenyl" refers to an alicyclic moiety having from three to six carbon atoms and having in addition one double bond. This term would include for example cyclopentenenyl or cyclohexenyl.

The term "heterocyclo ($C_{4-6}$) alkyl" refers to a saturated heterocyclic moiety having from three to six carbon atoms and one or more heteroatom from the group N, O, S and includes for example azetidinyl, pyrrolidinyl, tetrahydrofuranyl, piperidinyl and the like.

There term "aryl" means an optionally substituted phenyl or naphthyl group with the substituent(s) being selected, for example, from halogen, trifluoromethyl, $C_{1-6}$ alkyl, alkoxy, phenyl and the like.

The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benzyl or tert-butyl ester.

The term "heteroaryl" refers to aromatic ring systems of five to ten atoms or which at least one atom is selected from the group, O, N, or S and includes for example furanyl, thiophenyl, pyridyl, indolyl, quinolyl and the like.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2R^{22}$ where $R^{22}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trmethylbenzyloxymethyl or pivaloyloxymethyl group.

Compounds of the general formula (I) may be prepared by any suitable method known in the art and/or by the following processes, which itself forms part of the invention.

According to a second aspect of the invention, there is provided a process for preparing a compound of general formula (I) as defined above. It will be appreciated that where a particular stereoisomer of formula (I) is required, the synthetic processes described herein may be used with the appropriate homochiral starting material and/or isomers maybe resolved from mixtures using conventional separation techniques (eg. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, R, S, W, X, Y and Z are as defined above, otherwise indicated. It will be appreciated that functional groups, such as amino, hydroxyl or carboxyl groups, present in the various compounds decribed below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, P G M Wuts.

The process required for preparing compounds of general formula (I) comprises of:

deprotecting (for example by hydrolysis) a compound of general formula (II)

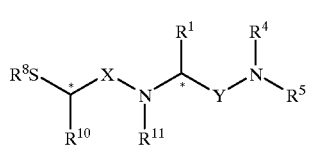

(II)

Wherein $R^8$ represents a suitable protecting group (eg tert-butyl, trityl, benzoyl or acetate).

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

When X and Y are C=O, intermediates of general formula (II) may be prepared by coupling an acid of formula (III)

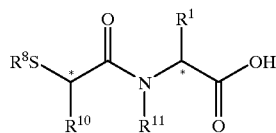

(III)

Wherein $R^1$, $R^{10}$ and $R^{11}$ are as defined above, or an active derivative thereof, with an amine of formula (IV)

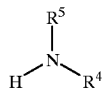

(IV)

Where $R^4$ and $R^5$ are defined previously.

Amines of formula (IV) may be commercially available or can be readily obtained from commercially available starting materials using methods known to those skilled in the art.

Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, eg. a cyclic ether such as tetrahydrofuran, an amide eg. a substituted amide such as dimethylformamide, or a halogenated hydrocarbon such as dichloromethane at a low temperature eg. –30° C. to ambient temperature, such as –20° C. to 0° C., optionally in the presence of as base, eg. an organic base such as an amine, eg. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (IV).

The acid of general formula (III) may be prepared by coupling an acid of formula (V), or an active derivative thereof

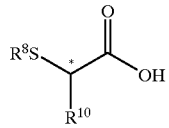

(V)

With an amine of formula (VI)

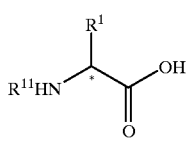

(VI)

followed by removal of any protecting groups.

Active derivates of acids for formula (V) include for example acid anhydrides or acid halides such as acid chlorides as outlined earlier.

α-Thioacetic acids and amino acids and their derivatives such as depicted by general formulae (V) and (VI) respectively can be obtained in optically pure or racemic form. In the homochiral form they provide asymmetric building blocks for the enantiospecific synthesis of compounds of general formula (I). Many of these derivatives can be readily obtained from commercially available starting materials using methods known to those skilled in the art. (See "The Practice of Peptide Synthesis" by M. Bodanszk et al, Springer Verlag, New York, 1984, P. L. Durette, WO92/21360).

As a further extension to the present invention compounds of general formula (II) or (V) may be prepared by nucleophilic substitution of compounds of general formula (VII) or (VIII) respectively.

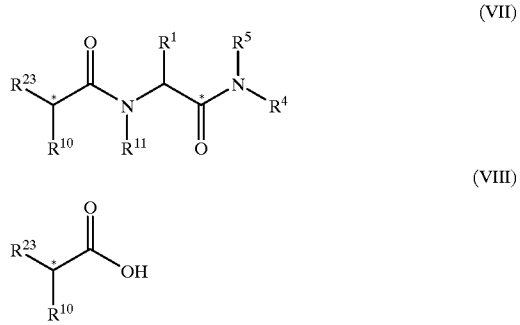

(VII)

(VIII)

Wherein $R^{23}$ represents a suitable leaving group (eg. a halogen such as bromide, or an alkylsulphonate ester such as methanesulphonate) with a thiol of general formula (IX)

$R^8SH$ (IX)

Wherein $R^8$ represents a suitable protecting group (eg. tert butyl, trityl, benzoyl or acetate), using standard conditions known to those skilled in the art as exemplified by C. Campion et al, WO 90/9005719.

Thiols of general formula (IX) may be obtained from commercially available starting materials using methods known to those skilled in the art. Many thiols of general formula (IX) are also commercially available.

Compounds of general formula (VII) may be prepared by coupling an acid of general formula (X)

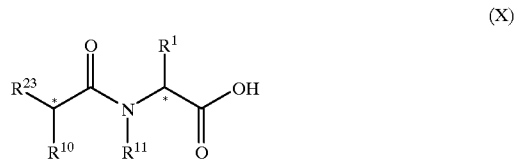

(X)

Wherein $R^{23}$, $R^{10}$ and $R^{11}$ are as defined above (or suitably protected versions thereof) or an active derivative thereof, with an amine of formula (IV) using similar coupling conditions to those described for the preparation of compounds of formula (II).

Carboxylic acids of the structure depicted in formulae (VIII) and (X) can be obtained in chiral or racemic form. Many of these derivatives can be readily obtained from commercially available starting materials using methods known to those skilled in the art (see C Campion et al WO 90/9005719).

Where $R^{11}$ is not H and amino acids of general formula (VI) are required, these may be prepared by the nucleophilic displacement of an alkylating agent of formula (XII) with an amine of formula (XIII)

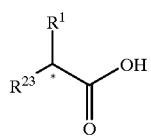

(XII)

(XIII)

wherein $R^{11}$ and $R^{23}$ have been defined previously.

Intermediates of formula (XII) may be prepared from amino acids of general formula (VI) by diazotisation under appropriate conditions.

Amines of formula (XIII) may be commercially available or can be readily obtained from commercially available starting materials using methods known to those skilled in the art.

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol—eg ethanol) of a compound of formula (I) wherein $R^8$ is a $C_{2-6}$ alkenyl group. A further example would include a compound of formula (I) wherein $R^8$ is a group $R^9$ CO may be prepared by acylation (using a suitable acid chloride $R^9$ COCl, in the presence of a base such as a triethylamine in a suitable solvent, such as a chlorinated solvent—eg dichloromethane) of a compound of formula (I) wherein $R^8$ is H.

Also compounds where X and Y are C=S may be prepared by thioamidation, for intance with Lawesson's Reagent, of compounds where X and Y are C=O.

Any mixtures of final products or intermediates obtained can be separated on the basis of the pysico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNF release. The activity and selectivity of the compounds may be determined by use of the appropriate enzyme inhibition test, for example as described in Example A hereinafter.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atherosclerosis, congestive heart failure, stroke, vasculitis, Crohn's disease, ulcerative colitis, multiple sclerosis, periodontitis, gingivitis and those involving tissue breakdown such as bone resportion, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema and anaphylaxis.

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compunds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinylpyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters dervied from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by. suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragacanth, naturally-occuring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms per patient per day). for example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following non-limiting Examples are intended to illustrate the preparation of compounds of Formula (I), and as such are not intended to limit the invention as set forth in the claims.

In the Examples, the following abbreviations are used:
RT Room temperature
DCC Dicyclohexylcarbodiimide
EDC 1-(3-Dimethylaminopropyl)-3-ethyl carbodiimide hydrochloride
TNFα Tumour necrosis factor α
LPS Lipopolysaccharide
ELISA Enzyme linked immunosorbent assay
Intermediate 1
  5-Phihalimidopentanoic acid
  N-Carboethoxyphthalimide (17.2 g, 78,6 mmol) was added in one portion to a vigorously stirred solution of 5-aminovaleric acid (9.26 g, 79.1 mmol) and sodium carbonate (8.45 g, 79.9 mmol) in water (300 ml ) at RT. The Mixture was stirred until essentially all the solid material had dissolved (30 min), then it was filtered. The filtrate was acidified to pH1 with 6M hydrochloric acid (ca. 20 ml) and the white precipitate was collected by filtration and washed thoroughly with water (150 ml). The solid was dried in air, then in vacua to give the title compound as a colourless solid (13.5 g, 69%).
  $^1$H NMR (250 MHz; CDCl$_3$, Ref., TMS) d 1.6–1.8 (4H, m), 2.20 (2H, t), 3,85(2H, t), 7.70–7.75 (2H, m), 7.85–7.95 (2H, m) and 10.2 (1H, br s).
Intermediate 2
  (RS) 2-Bromo-5-phthalimidopentanoic acid
  Intermediate 1 (5.0 g, 20.2 mmol) and thionyl chloride (10 ml) were heated together at 65° C. for 30 min. N-Bromosuccinimide (5.4 g, 30.3 mmol) and further thionyl chloride (10 ml) were added, plus 48% aqueous HBr (1 drop). The solution was heated at 70–80° C. for 4 h. Further N-bromosuccinimide (2.7 g, 15.2 mmol) was added and the mixture was heated at 70–80° C. for another 2 h. Excess thionyl chloride was removed by evaporation under reduced pressure and the oily residue diluted with dry tetahydrofuran (200 ml) and water (200 ml). The mixture was then treated cautiously with solid sodium bicarbonate to pH 7–8 then stirred overnight at RT. Excess tetahydrofuran was removed in vacua and the residue washed with dichloromethane (3×300 ml). The aqueous portion was then cautiously acidified to pH 1 using 6M hydrochloric acid and extracted with dichloromethane (4×200 ml). The combined extracts were then washed with water (2×400 ml) and brine (400 ml), dried (MgSO$_4$) and evaporated in vacuo to provide the product (4.7 g, 71%) as a fawn solid,
  TLC R$_f$ 0.47 (EtOAc)
Intermediate 3
  (RS) 2-Acetylsulphanyl-5-phthalimidopentanoic acid
  A solution of intermediate 2 (3.0 g, 9.2 mmol) in methanol (30 ml) was treated with potassium thioacetate (1.05 g, 9.2 mmol) and the mixture stirred at RT overnight. The mixture was evaporated in vacuo, the residue dissolved in dichloromethane (100 ml) then the solution washed with water (2×50 ml), dried (MgSO$_4$) and evaporated in vacuo to provide the product (2.4 g, 81%) as a pale yellow foam.
  TLC R$_f$ 0.43 (EtOAc)
Intermediate 4
  2-Acetylsulphanyl-5-phthalimidopentanoyl-L-leucine 1,1-dimethylethyl ester
  EDC (3.64 g, 19 mmol) was added to a stirred mixture of L-leucine 1,1-dimethylethyl ester (3.93 g, 17.6 mmol), N-hydroxybenzotriazole (2.62 g, 19.4 mmol), triethylamine (2.51 ml, 18 mmol) and intermediate 3 (5.94 g, 18.5 mmol) in dry tetrahydrofuran (200 ml). The mixture was stirred overnight then the solvent removed in vacuo and the residue partitioned between water (100 ml) and ethyl acetate (100 ml). The aqueous portion was then extracted with ethyl acetate (2×50 ml), the combined extracts washed with water (2×100 ml) and brine (100 ml), dried (MgSO$_4$) and evaporated in vacuo to a colourless oil.
  Purification by column chromatography eluting with hexane/ethyl acetate (2:1) provided the title compound (6.6 g, 77%) as a white solid, a 1:1 mixture of diastereoisomers.
  TLC R$_f$ 0.42 (EtOAc/Hexane (1:1))
Intermediate 5
  2-Acetylsulphanyl-5-phthalimidopentanoyl-L-leucine
  Trifluoroacetic acid (9.0 ml, 115 mmol) was added to a stirred solution of intermediate 4 (3.0 g, 6.1 mmol) in dry dichloromethane (40 ml) and the mixture stirred at RT overnight. The mixture was concentrated in vacuo and the excess trifluoroacetic acid removed by azeotroping with heptane to provide the title compound (2.48 g, 94%) as a colourless foam, a 1:1 mixture of diastereoisomers.

TLC $R_f$ 0.42 (EtOAc/Hexane (3:2))

Intermediate 6

(3S)-(1,1-Dimethylethyloxy)carbonyl-hexahydropyridazine-3-carboxylicacid N-methyl amide Was prepared according to the method of C. E. Adams, et al, *Synth. Commun,* 1988, 18, 2225.

EXAMPLE 1

2-Acetylsulphanyl-5-phthalimidopentanoyl-L-leucine N-(2-phenylethyl)amide

A solution of intermediate 5 (400 mg, 0.92 mmol), N-hydroxybenzotriazole (137 mg, 1.01 mmol) and phenethylamine (116 μl, 0.92 mmol) in dry tetrahydrofuran (20 ml) was treated at RT with EDC (194 mg, 1.01 mmol) and the mixture stirred overnight. The mixture was diluted with ethyl acetate (80 ml) and the resulting solution washed with 2M hydrochloric acid (50 ml), 8% aqueous sodium bicarbonate (50 ml), water (50 ml) and brine (50 ml), dried ($MgSO_4$) and evaporated in vacuo to provide a colourless oil.

Purification by column chromatography eluting with 3% methanol in dichloromethane furnished the title compound (440 mg, 89%) as a white solid.

TLC $R_f$ 0.49 (3% MeOH—$CH_2Cl_2$)

$C_{29}H_{35}N_3O_5S[537.7]$, $MH^+$ 538

Similarly prepared were:

EXAMPLE 2

2-Acetylsulphanyl-5-phthalimidopentanoyl-L-leucine N-(2-phenylmethyl)amide

From intermediate 5 and benzylamine, as a white solid (460 mg, 76%).

TLC $R_f$ 0.35 (5% MeOH—$CH_2Cl_2$)

$C_{28}H_{33}N_3O_5S[523.7]$, $MH^+$ 524

EXAMPLE 3

2-Acetylsulphanyl-5-phthalimidopentanoyl-L-leucine N-[2-(1H-indol-3-yl)ethyl]amide From intermediate 5 and tryptamine, as a pale yellow solid (1.36 g, 52%).

TLC $R_f$ 0.27 (5% MeOH—$CH_2Cl_2$)

$C_{31}H_{36}N_4O_5S[576.7]$, $MH^+$ 577

EXAMPLE 4

2-Acetylsulphanyl-5-phthalimidopentanoyl-L-leucine N-[2-(5-methoxy-1H-indol-3-yl)ethyl]amide From intermediate 5 and 5-methoxytryptamine, as a pale yellow solid (447 mg, 67%).

TLC $R_f$ 0.40 (5% MeOH—$CH_2Cl_2$)

$C_{32}H_{38}N_4O_6S[606.7]$, $MH^+$ 607

EXAMPLE 5

2-Acetylsulphanyl-5-phthalimidopentanoyl-L-leucine N-[2-(6-methoxy-1H-indol-3-yl)ethyl]amide From intermediate 5 and 6-methoxytryptamine, as a pale yellow solid (333 mg, 50%).

TLC $R_f$ 0.42 (5% MeOH—$CH_2Cl_2$)

$C_{32}H_{38}N_4O_5S[606.7]$, $MH^+$ 607

EXAMPLE 6

2-Acetylsulphanyl-5-phthalimidopentanoyl-L-leucine N-[2-(2-pyridyl)ethyl]amide

From intermediate 5 and 2-pyridylethylamine, as a white solid (347 mg, 63%).

TLC $R_f$ 0.35 (5% MeOH—$CH_2C_2$)

$C_{28}H_{34}N_4O_5S[538.7]$, $MH^+$ 539

EXAMPLE 7

2-Acetylsulphanyl-5-phthalimidopentanoyl-L-leucine N-[2-(methoxycarbonyl)ethyl]amide From intermediate 5 and 2-aminopropanoic acid methyl ester, as a white solid (355 mg, 53%).

TLC $R_f$ 0.45 (5% MeOH—$CH_2Cl_2$)

$C_{25}H_{33}N_3O_7S[519.6]$, $MH^+$ 520

The following examples were also prepared by the method outlined above:

EXAMPLE 8

2-Acetylsulphanyl-5-phthalimidopentanoyl-L-leucine N-[4-morpholino]amide

EXAMPLE 9

2-Acetylsulphanyl-5-phthalimidopentanoyl-L-leucine N-[(4-methyl-3-oxo)piperazino]amide

EXAMPLE 10

2-Acetylsulphanyl-5-phthalimidopentanoyl-L-leucine N-[(4acetyl)piperazino]amide

EXAMPLE 11

2-Acetylsulphanyl-5-phthalimidopentanoyl-L-leucine-N-[(2-acetylamino)ethyl]amide

EXAMPLE 12

2-Acetylsulphanyl-5-phthalimidopentanoyl-L-leucine N-[2-(4-morpholino)ethyl]amide

EXAMPLE 13

2-Acetylsulphanyl-5-phthalimidopentanoyl-L-leucine N-[3-(1-imidazolyl)propyl]amide

EXAMPLE 14

2-Acetylsulphanyl-5-phthalimidopentanoyl-L-leucine N-[3-(2-oxo-1-pyrrolidinyl)propyl]amide

EXAMPLE 15

2-Acetylsulphanyl-5-phthalimidopentanoyl-L-leucine N-[2-(1-oxo-1-phenyl)ethyl]amide

EXAMPLE 16

2-Acetylsulphanyl-5-phthalimidopentanoyl-L-leucine N-[4-(sulphonamido)phenyl]amide

EXAMPLE 17

2-Acetylsulphanyl-5-phthalimidopentanoyl-L-(S-methyl) cysteinyl N-(2-phenylethyl)amide

EXAMPLE 18

2-Acetylsulphanyl-5-phthalimidopentanoyl-L-(S-methyl) cysteinyl N-[4-morpholino]amide

EXAMPLE 19

2-Acetylsulphanyl-5-phthalimidopentanoyl-L-(S-methyl) cysteinyl N-[4-methoxyphenyl]amide Also prepared was:

EXAMPLE 20

2-Acetylsulphanyl-5-phthalimidopentanoyl-L-(S-methyl) cysteinyl N-[(3S)-hexahydropyridazine]-3-carboxylic acid N-methyl amide From intermediate 6, as a colourless foam (45%) after removal of the tert-butyloxycarbonyl group with trifluoroacetic acid under standard conditions.

TLC $R_f$ 0.38 (5% MeOH—CH$_2$Cl$_2$)

EXAMPLE 21

2-Sulphanyl-5-phthalimidopentanoyl-L-leucine N-(2-phenylmethyl)amide

A solution of example 2 (299 mg, 0.57 mmol) in dry methanol (15 ml) was treated at RT with concentrated ammonia solution (1.0 ml) and the mixture stirred for 2 h. The solvent was removed in vacuo and the residue purified by column chromatography eluting with 3% methanol in dichloromethane to provide the tide compound (228 mg, 83%) as a white solid.

TLC $R_f$ 0.27 (5% MeOH—CH$_2$Cl$_2$)
$C_{26}H_{31}N_3O_4S$[481.6], MH$^+$ 482

Similarly prepared were:

EXAMPLE 22

2-Sulphanyl-5-phthalimidopentanoyl-L-leucine N-(2-phenylethyl)amide

From example 1, as a white solid (247 mg, 95%)
TLC $R_f$ 0.31 (5% MeOH—CH$_2$Cl$_2$)
$C_{27}H_{33}N_3O_4S$[495.7], MH$^+$ 496

EXAMPLE 23

2-Sulphanyl-5-phthalimidopentanoyl-L-leucine N-[2-(1H-indol-3-yl)ethyl]amide

From example 3, as a pale yellow solid (120 mg, 45%).
TLC $R_f$ 0.55 (5% MeOH—CH$_2$Cl$_2$)
$C_{29}H_{34}N_4O_4S$[534.7], MH$^+$ 535

EXAMPLE 24

2-Sulphanyl-5-phthalimidopentanoyl-L-leucine N-[2-(5-methoxy-1H-indol-3-yl)ethyl]amide From example 4, as a near white solid (150 mg, 53%).
TLC $R_f$ 0.35 (5% MeOH—CH$_2$Cl$_2$)
$C_{30}H_{36}N_4O_5S$[564.7], MH$^+$ 565

EXAMPLE 25

2-Sulphanyl-5-phthalimidopentanoyl-L-leucine N-[2-(6-methoxy-1H-indol-3-yl)ethyl]amide From example 5, as a pale yellow solid (160 mg, 56%).
TLC $R_f$ 0.42 (5% MeOH—CH$_2$Cl$_2$)
$C_{30}H_{36}N_4O_5S$[564.7], MH$^+$ 565

EXAMPLE 26

2-Sulphanyl-5-phthalimidopentanoyl-L-leucine N-[2-(2-pyridyl)ethyl]amide

From example 6, as a white solid (155 mg, 69%).
TLC $R_f$ 0.35 (5% MeOH—CH$_2$Cl$_2$)
$C_{26}H_{32}N_4O_4S$[496.6], MH$^+$ 497

EXAMPLE 27

2-Sulphanyl-5-phthalimidopentanoyl-L-leucine N-[2-(methoxycarbonyl)ethyl]amide

From example 7, as a white solid (110 mg, 58%).
TLC $R_f$ 0.43 (5% MeOH—CH$_2$Cl$_2$)
$C_{23}H_{31}N_3O_6S$[477.5], MH$^+$ 478

EXAMPLE 28

2-Sulphanyl-5-phthalimidopentanoyl-L-(S-methyl)cysteinyl N-(2-phenylethyl)amide

From example 17, as a white solid (428 mg, 88%).
TLC $R_f$ 0.47 (5% MeOH—CH$_2$Cl$_2$)

EXAMPLE 29

2-Sulphanyl-5-phthalimidopentanoyl-L-(S-methyl)cysteinyl N-[4-morpholino]amide

From example 18, as a white solid (367 mg, 85%).
TLC $R_f$ 0.42 (5% MeOH—CH$_2$Cl$_2$)

EXAMPLE 30

2-Sulphanyl-5-phthalimidopentanoyl-L-(S-methyl)cysteinyl N-[4-methoxyphenyl]amide From example 19, as a white solid (300 mg, 80%).
TLC $R_f$ 0.47 (5% MeOH—CH$_2$Cl$_2$)

EXAMPLE 31

2-Sulphanyl-5-phthalimidopentanoyl-L-(S-methyl)cysteinyl N-[(3S)-hexahydro pyridazine]-3-carboxylic acid N-methyl amide From example 20, as a white solid (20 mg, 36%).
TLC $R_f$ 0.37 (5% MeOH—CH$_2$Cl$_2$)

EXAMPLE A

Collagenase inhibition activity

The potency of compounds of general formula (I) to act as inhibitors of collagenase was determined by the procedure of Cawston and Barrett, (Anal. Biochem., 99:340–345, 1979) whereby a 1 mM solution of the inhibitor being tested or dilutions thereof was incubated at 37° C. for 16 hours with collagen and collagenase (buffered with 50 mM Tris, pH 7.6 containing 5 mM CaCl$_2$, 0.05% Brij 35, 60 mM NaCl and 0.02% NaN$_3$). The collagen was acetylated $^3$H or $^{14}$C-collagen prepared by the method of Cawston and Murphy (Methods in Enzymolgy, 80:711, 1981). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported as that inhibitor concentration effecting 50% inhibition of the collagenase (IC$_{50}$).

EXAMPLE B

Stromelysin inhibition activity

The potency of compounds of general formula (I) to act as inhibitors of stromelysin was determined using the procedure of Nagase et al (Methods in Enzymology Vol 254, 1994), whereby a 0.1 mM solution of the inhibitor being tested or dilutions thereof was incubated at 37° C. for 16 hours with stromelysin and $^3$H transferrin (buffered with 50 mM Tris, pH 7.6 containing 10 mM CaCl$_2$, 150M NaCl, 0.05% Brij, 35, and 0.02% NaN$_3$). The transferrin was carboxymethylated with $^3$H iodoacetic acid. The stromelysin activity in the presence of 1 mM, or a dilution thereof, was compared to activity in a control devoid of inhibitor and the results reported as that inhibitor concentration effecting 50% inhibition of the stromelysin (IC$_{50}$)

EXAMPLE C

Gelatinase inhibition activity

The potency of the compounds of general formula (I) to act as inhibitors of gelatinase was determined using the procedure of Harris & Krane (Biochem Biophys. Acta, 258:566–576, 1972), whereby a 1 mM solution of the inhibitor being tested or dilutions thereof was incubated at 37° C. for 16 hours with gelatinase and heat denatured $^3$H or $^{14}$C-acetylated collagen (buffered with 50 mM Tris, pH 7.6 containing 5 mM $CaCl_2$, 0.05% Brij 35 and 0.02% $NaN_3$). The $^3$H or $^{14}$C gelatin was prepared by denaturing $^3$H or $^{14}$C-collagen produced according to the method of Cawston and Murphy (Methods in Enzymology, 80:711, 1981) by incubation at 60° C. for 30 minutes. Undigested gelatin was precipitated by addition of trichloroacetic acid and centrifugation. The gelatinase activity in the presence of 1 mM, or dilution thereof, was compared to the activity in a control devoid of inhibitor and results reported as that inhibitor concentration effecting 50% inhibition of the gelatinase ($IC_{50}$).

EXAMPLE D

MMP inhibition activity-fluorimetric assay

The potency of compounds of general formula (I) to act as inhibitors of collagenase-1 (MMP-1), collagenase-2 (MMP-8), gelatinase-A (MMP-2), gelatinase-B (MMP-9) and stromelysin-1 (MMP-3) was determined using the following procedure: Inhibitors are dissolved in dimethylsulphoxide containing 0.02% β-mercaptoethanol and serial dilutions are prepared. Activated enzyme is incubated in assay buffer containing 50 mM Tris, pH 7.4, 5 mM $CaCl_2$, 0.002% $NaN_3$ and Brij 35 in the presence and absence of inhibitor. Samples are preincubated at 37° C. for 15 minutes before the addition of the fluorimetric substrate (Mca-Pro-Leu-Dpa-Ala-Arg-$NH_2$) to a final concentration of 10 $\mu$M. The assay is incubated for 90 minutes at 37° C. and then read in a Fluoroscan II at $\lambda_{ex}$ (355 nm) and $\lambda_{em}$ (460 nm). The enzyme activity was compared to activity in a control devoid of inhibitor and the results reported as that inhibitor concentration effecting 50% inhibition of the stromelysin ($IC_{50}$).

EXAMPLE E

Inhibition of TNFα production

The potency of the compounds of general formula (I) to act as inhibitors of the production of TNFα was determined using the following procedure. A 1 mM solution of the inhibitor being tested or dilutions thereof was incubated at 37° C. in an atmosphere of 5% $CO_2$ with THP-1 cells (human monocytes) suspended in RPM1 1640 medium and 20 $\mu$M β-mercaptoethanol at a cell density of 1×10$^6$/ml and stimulated with 5 $\mu$g/ml final concentration of LPS. After 18 hours the supernatant is assayed for the levels of TNFα using a commercially available ELISA kit (R & D Systems).

The activity in the presence of 0.1 mM inhibitor or dilutions thereof was compared to activity in a control devoid of inhibitor and results reported as that inhibitor concentration effecting 50% inhibition of the production of TNFα.

EXAMPLE F

Adjuvant arthritic rat model

Compounds of general formula (I) were evaluated in an adjuvant arthritis model in the rat based on the methods employed by B. B. Newbould (1963), Br. J. Pharmacol, 21, 127–136 and C. M. Pearson and F. D. Wood (1959), Arthritis Rheum, 2, 440–459. Briefly male Wistar rats (180–200 g) were injected at the base of the tail with Freund's adjuvant. Twelve days later the responding animals were randomised into experimental groups. Compounds of general formula (I) were dosed either orally as a suspension in 1% methyl cellulose or intraperitoneally in 0.2% carboxymethylcellulose from day 12 to the end of the experiment on day 22. Hind paw volumes were measured every two days from day 12 onwards and X-rays were taken of the hind feet on completion of the experiment. Results were expressed as the percent increase of foot volume over day 12 values.

EXAMPLE G

Mouse ovarian carcinoma xenograft model

Compounds of general formula (I) were evaluated in an ovarian carcinoma xenograft model of cancer, based on that described by B. Davies et al (1993), Cancer Research, 53, 2087–2091. This model, in brief, consists of inoculating female nu/nu mice with 1×10$^9$ OVCAR3-icr cells into the peritoneal cavity. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the number of peritoneal cells are counted and any solid tumour deposits weighed. In some experiments tumour development is monitored by measurement of tumour specific antigens.

EXAMPLE H

Rat mammary carcinoma model

Compounds of general formula (I) were evaluated in a HOSP.1 rat mammary carcinoma model of cancer (S. Eccles et al (1995), Cancer Research, in press). This model consists of the intravenous inoculation of female CBH/cbi rats with 2×10$^4$ tumour cells into the jugular vein. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the animals were killed, the lungs were removed and individual tumopurs counted after 20 hours fixation in Methacarn.

We claim:

1. A compound of the formula (I):

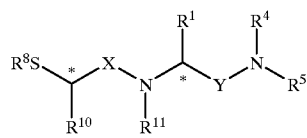

wherein:

X and Y are selected from C=O or C=S and may be the same or different; Y may also be $S(O)_m$ where m=1–2;

$R^1$ is a $C_{1-6}$ alkyl, $C_{2-6}$ alkenyl, aryl, $C_{1-6}$ alkyl-aryl, heteroaryl, $C_{1-6}$ alkyl-heteroaryl, cyclo ($C_{3-6}$) alkyl, $C_{1-6}$ alkyl-cyclo($C_{3-6}$)alkyl, heterocyclo($C_{1-6}$)alkyl, $C_{1-6}$ alkyl-heterocyclo($C_{4-6}$)alkyl, $C_{1-6}$ alkyl-$COR^2$, or $C_{1-6}$ alkyl-$AR^3$ group where A is O, $NR^3$ or $S(O)_n$ wherein n=0–2 and $R^3$ is H, $C_{1-4}$ alkyl, aryl, heteroaryl, $C_{1-4}$ alkyl-aryl or $C_{1-4}$ alkyl-heteroaryl; If A=$NR^3$ the groups $R^3$ may be the same or different;

$R^2$ is $OR^4$ or $N(R^4)_2$ where $R^4$ may be the same or different;

$R^4$ is H or $C_{1-4}$ alkyl;

$R^5$ is aryl (optionally substituted with $R^6$), heteroaryl (optionally substituted with $R^6$), $C_{1-4}$ alkyl-aryl (optionally substituted with $R^6$), $C_{1-4}$ alkyl-heteroaryl (optionally substituted with $R^6$), $C_{1-4}$ alkyl (substituted with $R^{21}$), cyclo($C_{3-6}$)alkyl (optioually substituted with $R^6$), $C_{1-4}$ alkyl-cyclo($C_{3-6}$)alkyl (substituted with $R^6$), heterocyclo($C_{4-6}$)alkyl (optionally substituted with $R^6$), or $C_{1-4}$ alkyl-hetorocyclo($C_{4-6}$)alkyl (optionally substituted with $R^6$);

$NR^4R^5$ may form a ring selected from the group consisting of pyrrolidine (optionally substituted with $R^6$), piperidine (optionally substituted with $R^6$), morpholine (optionally substituted with $R^6$) and piperazines of the type:

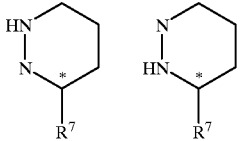

optionally substituted with $R^6$ at any available position;

$R^6$ is H, halogen, $C_{1-6}$ alkyl, aryl, heteroaryl, $OR^3$, $S(O)_n R^3$ where n=0–2, $NR^3R^7$, $COR^9$, $SO_2N(R^3)_2$ where $R^3$ may be the same or different, $CON(R_3)_2$ where $R^3$ may be the same or different, amidine or guanidine;

$R^7$ is $COR^9$, $CO_2R^{19}$, $SO_2R^9$ or $CO(NR^3)_2$ where $R^3$ may be the same or different;

$R^8$ is H or the group $COR^9$;

$R^9$ is $C_{1-4}$ alkyl, aryl, heteroaryl, $C_{1-4}$ alkyl-aryl or $C_{1-4}$ alkyl-heteroaryl;

$R^{10}$ is $C_{1-6}$ alkyl (optionally substituted with $R^{12}$) $C_{1-6}$ alkyl-aryl (optionally substituted with $R^{12}$), and $C_{1-6}$ alkyl-heteroaryl (optionally substituted with $R^{12}$);

$R^{11}$ is H, $C_{1-6}$ alkyl, (optionally substituted with $R^{12}$), aryl (optionally substituted with $R^{12}$), ($C_{1-6}$ alkyl-aryl (optionally substituted with $R^{12}$), heteroaryl (optionally substituted with $R^{12}$), $C_{1-6}$ alkyl-heteroaryl (optionally substituted with $R^{12}$), cyclo ($C_{3-6}$) alkyl (optionally substituted with $R^{12}$), $C_{1-6}$ alkyl-cyclo ($C_{3-6}$) alkyl (optionally substituted with $R^{12}$) or $C_{1-4}$ alkyl-heterocyclo ($C_{4-6}$) alkyl (optionally substituted with $R^{12}$);

$R^{12}$ is $COR^{13}$ or the group $AR^3$ where A is $NR^3$ wherein the groups $R^3$ may be the same or different, phthalimido or the groups:

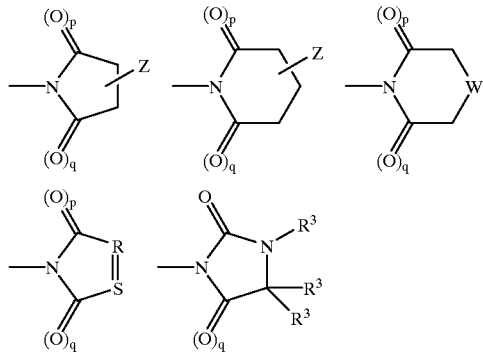

p and q may be 0 or 1 and may be the same or different;
R and S may be CH or N and may be the same or different;
W may be O, $S(O)_n$ where n=0–2 or $NR^{15}$;
Z may be H or $C_{0-4}$ alkyl-$R^{18}$ and may be attached to any available position on the ring;
$R^{13}$ is $OR^{20}$, $N(R^3)_2$ where $R^3$ may be the same or different, $C_{1-4}$ alkyl, aryl, $C_{1-4}$ alkyl-aryl, heteroaryl or $C_{1-4}$ alkyl-heteroaryl;

$R^{14}$ may be any group defined in $R^7$, $SO_2R^{16}$, or $COR^{16}$;

$R^{15}$ is H, $C_{1-4}$ alkyl, $COR^9$, $CO_2R^{19}$, $CON(R^3)_2$ where $R^3$ may be the same or different or $SO_2R^9$;

$R^{16}$ is $C_{1-4}$ alkyl (optionally substituted with $R^{17}$);

$R^{17}$ may be $CO_2R^3$, $CON(R^3)_2$ where $R^3$ are the same or different, $N(R^3)_2$ where $R^3$ are the same or different, $SO_2R^9$ or the groups:

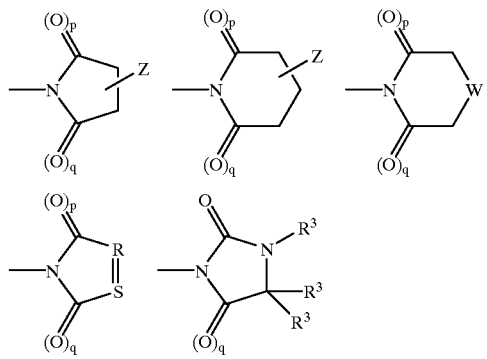

$R^{18}$ is $CO_2R^3$, $CON(R^3)_2$ where $R^3$ are the same or different, $N(R^3)_2$ where $R^3$ are the same or different, $NHCO_2R^{19}$, $NHSO_2R^9$ or $NHCOR^9$;

$R^{19}$ is $C_{1-4}$ alkyl, $C_{1-4}$ alkyl-aryl or $C_{1-4}$ alkyl-heteroaryl;

$R^{20}$ is H, $C_{1-4}$ alkyl, $C_{1-4}$ alkyl-aryl or $C_{1-4}$ alkyl-heteroaryl;

$R^{21}$ is $C_{1-6}$ alkyl, aryl, heteroaryl, $NR^3R^7$, $COR^9$, $SO_2N(R^3)_2$ where $R^3$ are the same or different;

and the salts, solvates and hydrates thereof.

2. The compound of claim 1, wherein X and Y are each C=O.

3. The compound of claim 1, wherein $R^1$ is a $C_{1-6}$ alkyl or $C_{1-6}$ alkyl-$AR^3$ group where A is O, $NR^3$ or $S(O)_n$ where n=0–2 and $R^3$ is H, $C_{1-4}$ alkyl, heteroaryl or aryl.

4. The compound of claim 1, wherein $R^4$ is H.

5. The compound of claim 1, wherein $R^5$ is aryl (optionally substituted with $R^6$), heteroaryl (optionally substituted with $R^6$), $C_{1-4}$ alkyl-aryl (optionally substituted with $R^6$), $C_{1-4}$ alkyl-heteroaryl (optionally substituted with $R^6$) or $C_{1-4}$ alkyl-heterocyclo($C_{4-6}$)alkyl (optionally substituted with $R^6$).

6. The compound of claim 1, wherein $R^6$ is H, halogen, $C_{1-6}$ alkyl, aryl, heteroaryl, $AR^3$, $NR^3R^7$, $COR^9$, $SO_2N(R^3)_2$ where $OR^3$ may be the same or different, $CON(R^3)_2$ where $R^3$ may be the same or different, amidine or guanidine.

7. The compound of claim 1, wherein $NR^4R^5$ is a ring which is pyrrolidine (optionally substituted with $R^6$), piperidine (optionally substituted with $R^6$), morpholine or optionally-substituted piperazine as defined in claim 1.

8. The compound of claim 1, wherein $R^7$ is $CO_2R^{19}$ or $CONHR^3$ where $R^{19}$ is H or $C_{1-4}$ alkyl.

9. The compound of claim 1, wherein $R^8$ is H or the group $COR^9$.

10. The compound of claim 1, wherein $R^9$ is $C_{1-4}$ alkyl or aryl.

11. The compound claim 1, wherein $R^{11}$ is H.

12. The compound of claim 1, wherein $R^{11}$ is H or alkyl optionally substituted with $R^{12}$.

13. The compound of claim 1, wherein $R^{13}$ is $OR^{20}$ or $N(R^3)_2$.

14. The compound of claim 1, wherein $R^{13}$ is $OR^{20}$, $N(R_3)_2$ where $R^3$ may be the same or different and $R^{20}$ is H or $C_{1-4}$ alkyl.

15. The compound of claim 1, wherein $R^1$ is not alkyl-$COR^2$, cycloalkyl, alkyl-cycloalkyl or alkyl-heterocycloalkyl, $R^1$ is H, and $R^{10}$ is $C_{6-10}$ aryl, $C_{5-10}$ heteroaryl, $C_{1-4}$ alkyl-$R^{12}$, alkyl-aryl $C_{1-4}$ alkyl-heteroaryl, cycloalkyl, cycloalkenyl or alkyl-cycloalkyl, any being optionally substituted by $R^{12}$.

16. The compound of claim 1, selected from the group consisting of

2-Acetylsulphanyl-5-phthalimidopentanoyl-L-leucine N-(2-phenylethyl)amide
2-Acetylsulphanyl-5-phthalimidopentanoyl-L-leucine N-(2-phenylmethyl)amide
2-Acetylsulphanyl-5-phthalimidopentanoyl-L-leucine N-[2-(1H-indol-3-yl)ethyl]amide
2-Acetylsulphanyl-5-phthalimidopentanoyl-L-leucine N-[2-(5-methoxy-1H-indol-3-yl)ethyl]amide
2-Acctylsulphanyl-5-phthalimidopentanoyl-L-leucine N-[2-(6-methoxy-1H-indol-3-yl)ethyl]amide
2-Acetylsulphanyl-5-phthalimidopentanoyl-L-leucine N-[2-(2-pyridyl)ethyl]amide
2-Acetylsulphanyl-5-phthalimidopentanoyl-L-leucine N-[2-(methoxycarbonyl)ethyl]amide
2-Sulphanyl-5-phthalimidopentanoyl-L-leucine N-(phenylmethyl)amide
2-Sulphanyl-5-phthalimidopentanoyl-L-leucine N-(2-phenylethyl)amide
2-Sulphanyl-5-phthalimidopentanoyl-L-leucine N-[2-(1H-indol-3-yl)ethyl]amide
2-Sulphanyl-5-phthalimidopentanoyl-L-leucine N-[2-(5-methoxy-1H-indol-3-yl)ethyl]amide
2-Sulphanyl-5-phthalimidopentanoyl-L-leucine N-[2-(6-methoxy-1H-indol-3-yl)ethyl]amide
2-Sulphanyl-5-phthalimidopentanoyl-L-leucine N-[2-(2-pyridyl)ethyl]amide and
2-Sulphanyl-5-phthalimidopentanoyl-L-leucine N-[2-(methoxycarbonyl)ethyl]amide.

17. A compound of claim 1, selected from the group consisting of

2-Acetylsulphanyl-5-phthalimidopentanoyl-L-leucine N-(4-morpholino)amide
2-Acetylsulphanyl-5-phthalimidepentanoyl-L-leucine N-(4-methyl-3-oxopiperazino)amide
2-Acetylsulphanyl-5-phthalimidopentanoyl-L-leucine N-(4-acetylpiperazino)amide
2-Acetylsulphanyl-5-phthalimidopentanoyl-L-leucine N-(2-acetylaminoethyl)amide
2-Acetylsulphanyl-5-phthalimidopentanoyl-L-leucine N-[2-(4-morpholino)ethyl]amide
2-Acetylsulphanyl-5-phthalimidopentanoyl-L-leucine N-[3-(1-imidazoyl)propyl]amide
2-Acetylsulphanyl-5-phthalimidopentanoyl-L-leucine N-[3-(2-oxo-1-pyrrolidinyl)propyl]amide
2-Acetylsulphanyl-5-phthalimidopentanoyl-L-leucine N-[2-(1-oxo-1-phenyl)ethyl]amide
2-Acetylsulphanyl-5-phthalimidopentanoyl-L-leucine N-(4-sulphonamidophenyl)amide and
2-Acetylsulphanyl-5-phthalimidopentanoyl-L-(S-methyl) cysteinyl N-(phenylmethyl)amide.

18. The compound of claim 1, selected from the group consisting of

2-Acetylsulphanyl-5-phthalimidopentanoyl-L-(S-methyl) cysteinyl N-(4-morpholino)-amide
2-Acetylsulphanyl-5-phthalimidopentanoyl-L-(S-methyl) cysteinyl N-(4-methoxyphenyl)amide
2-Acetylsulphanyl-5-phthalimidopentanoyl-L-(S-methyl) cysteinyl N-[(3S)-hexahydropyridazine]-3-carboxylic acid N-methylamide
2-Sulphanyl-5-phthalimidopentanoyl-L-(S-methyl) cysteinyl N-(2-phenylethyl)amide
2-Sulphanyl-5-phthalimidopentanoyl-L-(S-methyl) cysteinyl N-(4-morpholino)amide
2-Sulphanyl-5-phthalimidopentanoyl-L-(S-methyl) cysteinyl N-(4-methoxyphenyl)amide and
2-Sulphanyl-5-phthalimidopentanoyl-L-(S-methyl) cysteinyl N-[(3S)-hexahydropyridazine]-3-carboxylic acid N-methylamide.

19. The compound of claim 1, in the form of a single enantiomer or diastereomer, or a mixture of such isomers.

20. The pharmaceutical composition comprising a compound of claim 1, and a pharmaceutically-acceptable diluent or carrier.

21. A method for the treatment of a condition associated with matrix metalloproteinases or that is mediated by TNFα, comprising administering an effective amount of the compound of claim 1 to a person or animal in need of such treatment.

22. The method according to claim 21, wherein the condition is selected from the group consisting of cancer, inflammation and inflammatory diseases, tissue degeneration, periodontal disease, ophthalmological disease, dermatological disorders, fever, cardiovascular effects, haemorrhage, coagulation and acute phase response, cachexia and anorexia, acute infection, HIV infection, shock states, graft versus host reactions, autoimmune disease, reperfusion injury, meningitis and migraine.

23. The method according to claim 21, wherein the condition is selected from the group consisting of tumour growth, angiogenesis, tumour invasion and spread, metastases, malignant ascites and malignant pleural effusion.

24. The method according to claim 21, wherein the condition is selected from the group consisting of rheumatoid arthritis, osteoarthritis, osteoporosis, asthma, multiple sclerosis, neurodegeneration, Alzheimer's, stroke, vascutltis, Crohn's disease and ulcerative colitis.

25. The method according to claim 21, wherein the condition is selected from the group consisting of corneal ulceration, retinopathy and surgical wound healing.

26. The method according to claim 21, wherein the condition is selected from the group consisting of psoriasis, atopic dermatitis, chronic ulcers and epidermolysis bullosa.

27. The method according to claim 21, wherein the condition is selected from the group consisting of periodontitis and gingivitis.

28. The method according to claim 21, wherein the condition is selected from the group consisting of rhinitis, allergic conjunctivitis, eczema and anaphylaxis.

29. The method according to claim 21, wherein the condition is selected from the group consisting of atherosclerosis and congestive heart failure.

* * * * *

UNITED STATES PATENT AND TRADEMARK OFFICE
CERTIFICATE OF CORRECTION

PATENT NO. : 5,994,293
DATED : November 30, 1999
INVENTOR(S) : Andrew Douglas Baxter, et. al.

It is certified that error appears in the above-identified patent and that said Letters Patent is hereby corrected as shown below:

Column 24, line 54: "heterocyclo $(C_{1-6})$" should read --heterocyclo $(C_{4-6})$--.

Column 24, line 57: "wherein n=0-2 and $R^3$" should read --where n=0-2 and $R^3$--.

Column 24, line 55: "$C_{1-6}$, alkyl-$COR^2$," should read --$C_{1-6}$ alkyl-$COR^2$,--.

Column 24, line 67: "(optioually" should read --(optionally--.

Column 25, line 21: "$CON(R_3)_2$" should read --$CON(R^3)_2$--.

Column 25, line 32: "$(C_{1-6}$" should read --$C_{1-6}$--.

Column 26, line 48: "where $OR^3$" should read --where $R^3$--.

Col. 26, line 47 "$AR^3$" should read – $OR^3$ --.

Signed and Sealed this

First Day of May, 2001

Attest:

NICHOLAS P. GODICI

Attesting Officer    Acting Director of the United States Patent and Trademark Office